United States Patent
Sumiyoshi (10) Patent No.: US 10,317,380 B2
(45) Date of Patent: Jun. 11, 2019

(54) CHROMATOGRAPH MASS SPECTROMETER AND PROGRAM

(71) Applicant: SHIMADZU CORPORATION, Kyoto-shi, Kyoto (JP)

(72) Inventor: Takashi Sumiyoshi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 348 days.

(21) Appl. No.: 15/322,770

(22) PCT Filed: Jul. 3, 2014

(86) PCT No.: PCT/JP2014/067811
§ 371 (c)(1),
(2) Date: Dec. 29, 2016

(87) PCT Pub. No.: WO2016/002046
PCT Pub. Date: Jan. 7, 2016

(65) Prior Publication Data
US 2017/0138916 A1    May 18, 2017

(51) Int. Cl.
*G01N 30/86* (2006.01)
*G01N 30/72* (2006.01)
(Continued)

(52) U.S. Cl.
CPC ......... *G01N 30/8696* (2013.01); *G01N 30/72* (2013.01); *G01N 30/7233* (2013.01);
(Continued)

(58) Field of Classification Search
USPC ............................................... 250/281, 282
See application file for complete search history.

(56) References Cited

U.S. PATENT DOCUMENTS

| 8,168,942 | B2 * | 5/2012 | Sumiyoshi | ............. | G01N 27/62 250/281 |
| 8,735,809 | B2 * | 5/2014 | Sumiyoshi | ............. | H01J 49/02 250/281 |
| 2015/0247829 | A1 * | 9/2015 | Sumiyoshi | ......... | G01N 30/8651 250/288 |

FOREIGN PATENT DOCUMENTS

| JP | 2003-172726 A | 6/2003 |
| JP | 2012-132799 A | 7/2012 |

OTHER PUBLICATIONS

International Search Report for PCT/JP2014/067811 dated Sep. 30, 2014.
(Continued)

*Primary Examiner* — Kiet T Nguyen
(74) *Attorney, Agent, or Firm* — Sughrue Mion, PLLC (57) ABSTRACT

A chromatograph mass spectrometer has a function that: based on a compound table in which an elution time range and a measurement ion is described for respective compounds, divides an overall measurement time into multiple segments and assigns one or more compounds to each segment; determines an event time for each compound by dividing a previously given measurement loop time in accordance with a number of compounds belonging to the respective segments; and determines a dwell time, which is a data collection time for each ion, based on the event time and the number of ions to be measured for each compound; the chromatograph mass spectrometer allowing an analysis operator to designate whether or not to perform a high-sensitivity analysis for each compound.

9 Claims, 7 Drawing Sheets

(51) Int. Cl.
*H01J 49/00* (2006.01)
*H01J 49/04* (2006.01)

(52) U.S. Cl.
CPC ...... *G01N 30/8658* (2013.01); *H01J 49/0031* (2013.01); *H01J 49/0422* (2013.01); *G01N 30/86* (2013.01)

(56) References Cited

OTHER PUBLICATIONS

Written Opinion for PCT/JP2014/067811 dated Sep. 30, 2014. [PCT/ISA/237].

\* cited by examiner

| No. | COMPOUND NAME | SEG-MENT | MEASUREMENT START TIME (min) | MEASUREMENT END TIME (min) | EVENT TIME (msec) | QUANTITATIVE ION m/z-1 | CONFIRMATION ION m/z-2 | CONFIRMATION ION m/z-3 | Dwell TIME (msec) |
|---|---|---|---|---|---|---|---|---|---|
| 1 | A | 1 | 9.5 | 10.8 | 60 | 150 | 160 | 170 | 19 |
| 2 | B | 1 | 9.5 | 10.8 | 180 | 200 | 210 | 220 | 59 |
| 3 | C | 1 | 9.5 | 10.8 | 60 | 250 | 260 | 270 | 19 |
| 4 | D | 2 | 10.8 | 12.0 | 300 | 160 | 306 | 235 | 99 |
| 5 | E | 3 | 12.0 | ⋮ | ⋮ | 410 | 420 | 430 | ⋮ |
| ⋮ | ⋮ | ⋮ | ⋮ | ⋮ | ⋮ | ⋮ | ⋮ | ⋮ | ⋮ |

Fig. 6

| No. | COMPOUND NAME | RETENTION TIME(min) | PROCESS TIME(min) | QUANTITATIVE ION m/z-1 | CONFIRMATION ION m/z-2 | CONFIRMATION ION m/z-3 | HIGH SENSITIVITY MODE | | |
|---|---|---|---|---|---|---|---|---|---|
| 1 | A | 10.0 | ±0.5 | 150 | 160 | 170 | ☐ | ☐ | ☐ |
| 2 | B | 10.1 | ±0.5 | 200 | 210 | 220 | ☑ | ☐ | ☐ |
| 3 | C | 10.2 | ±0.5 | 250 | 260 | 270 | ☐ | ☐ | ☐ |
| 4 | D | 11.4 | ±0.5 | 160 | 306 | 235 | ☐ | ☐ | ☐ |
| 5 | E | 12.6 | ±0.5 | 410 | 420 | 430 | ☐ | ☐ | ☐ |
| ⋮ | ⋮ | ⋮ | ⋮ | ⋮ | ⋮ | ⋮ | | | |

MEASUREMENT LOOP TIME  300  msec
IMPROVEMENT RATIO  3  FOLD

Auto-Create

Fig. 7

| No. | COMPOUND NAME | SEG-MENT | MEASUREMENT START TIME(min) | MEASUREMENT END TIME(min) | EVENT TIME (msec) | QUANTITATIVE ION m/z-1 | CONFIRMATION ION m/z-2 | CONFIRMATION ION m/z-3 | DWELL TIME (msec) | | |
|---|---|---|---|---|---|---|---|---|---|---|---|
| | | | | | | | | | m/z-1 | m/z-2 | m/z-3 |
| 1 | A | 1 | 9.5 | 10.8 | 100 | 150 | 160 | 170 | 32.3 | 32.3 | 32.3 |
| 2 | B | 1 | 9.5 | 10.8 | 100 | 200 | 210 | 220 | 58.2 | 19.4 | 19.4 |
| 3 | C | 1 | 9.5 | 10.8 | 100 | 250 | 260 | 270 | 32.3 | 32.3 | 32.3 |
| 4 | D | 2 | 10.8 | 12.0 | 300 | 160 | 306 | 235 | 99.0 | 99.0 | 99.0 |
| 5 | E | 3 | 12.0 | ⋮ | ⋮ | 410 | 420 | 430 | ⋮ | ⋮ | ⋮ |
| ⋮ | ⋮ | ⋮ | ⋮ | ⋮ | ⋮ | ⋮ | ⋮ | ⋮ | ⋮ | ⋮ | ⋮ |

Fig. 8

| No. | COMPOUND NAME | RETENTION TIME(min) | PROCESS TIME (min) | QUANTITATIVE ION m/z-1 | CONFIRMATION ION m/z-2 | CONFIRMATION ION m/z-3 |
|---|---|---|---|---|---|---|
| 1 | A | 10.0 | ±0.5 | 150 | 160 | 170 |
| 2 | B | 10.1 | ±0.5 | 200 | 210 | 220 |
| 3 | C | 10.2 | ±0.5 | 250 | 260 | 270 |
| 4 | D | 11.4 | ±0.5 | 160 | 306 | 235 |
| 5 | E | 12.6 | ±0.5 | 410 | 420 | 430 |
| ⋮ | ⋮ | ⋮ | ⋮ | ⋮ | ⋮ | ⋮ |

MEASUREMENT LOOP TIME  300  msec

Auto-Create

| No. | COMPOUND NAME | SEG-MENT | MEASUREMENT START TIME(min) | MEASUREMENT END TIME(min) | EVENT TIME (msec) | QUANTITATIVE ION m/z-1 | CONFIRMATION ION m/z-2 | CONFIRMATION ION m/z-3 | Dwell TIME (msec) |
|---|---|---|---|---|---|---|---|---|---|
| 1 | A | 1 | 9.5 | 10.8 | 100 | 150 | 160 | 170 | 32 |
| 2 | B | 1 | 9.5 | 10.8 | 100 | 200 | 210 | 220 | 32 |
| 3 | C | 1 | 9.5 | 10.8 | 100 | 250 | 260 | 270 | 32 |
| 4 | D | 2 | 10.8 | 12.0 | 300 | 160 | 306 | 235 | 99 |
| 5 | E | 3 | 12.0 | ⋮ | ⋮ | 410 | 420 | 430 | ⋮ |
| ⋮ | ⋮ | ⋮ | ⋮ | ⋮ | ⋮ | ⋮ | ⋮ | ⋮ | ⋮ |

Fig. 12

CHROMATOGRAPH MASS SPECTROMETER AND PROGRAM

CROSS REFERENCE TO RELATED APPLICATIONS

This application is a National Stage of International Application No. PCT/JP2014/067811 filed Jul. 3, 2014, the contents of all of which are incorporated herein by reference in their entirety.

TECHNICAL FIELD

The present invention relates to a chromatograph mass spectrometer, such as a gas chromatograph mass spectrometer (GC/MS) or a liquid chromatograph mass spectrometer (LC/MS), which is a combination of a chromatograph and a mass spectrometer. More specifically, the present invention relates to a chromatograph mass spectrometer which performs selected ion monitoring (SIM) measurement, multiple reaction monitoring (MRM) measurement (also called "selection reaction monitoring (SRM) measurement"), or other similar measurements for known compounds in the mass spectrometer.

BACKGROUND ART

Chromatograph mass spectrometers combining a chromatograph, such as a gas chromatograph (GC) or a liquid chromatograph (LC), and a mass spectrometer, such as a quadrupole mass spectrometer, are widely used to perform qualitative or quantitative analyses of various components contained in a sample. When performing a quantitative analysis of known compounds using a chromatograph mass spectrometer, an SIM measurement method is typically used which selectively and repeatedly detects only ions having one or more specific mass-to-charge ratios (m/z) that are designated in advance.

When a known compound is quantitatively analyzed using a chromatograph mass spectrometer including a chromatograph, such as a GC or an LC, and a triple quadrupole mass spectrometer, an MRM measurement method is used. According to this method, an ion (precursor ion) having a specific mass-to-charge ratio is selected by a first-stage quadrupole mass filter, the ion is then fragmented by collision-induced dissociation (CID) in a collision cell, and an ion having a specific mass-to-charge ratio among the product ions generated by the fragmentation is selected by a second-stage quadrupole mass filter, and the selected ion is detected. The MRM measurement method is advantageous in that the influence of irrelevant substances can be removed by the quadrupole mass filters at the two stages, so that the SN ratio of the detection signal is improved and a higher level of sensitivity is achieved in quantitative determinations.

When performing quantitative analysis through either SIM measurement or MRM measurement using a chromatograph mass spectrometer, the value of mass-to-charge ratios corresponding to target compounds is required to be set in conformity with the retention times of the target compounds as one measurement condition. For example, chromatograph mass spectrometers described in Patent Literatures 1 and 2 have a function of automatically creating a parameter table representing measurement conditions. After an analysis operator creates a compound table including information relating to measurement target compounds, the parameter table is automatically created based on the information described in the compound table. Such an automatic parameter table creation function according to a conventional chromatograph mass spectrometer will be described with reference to a specific example.

Figure 8:
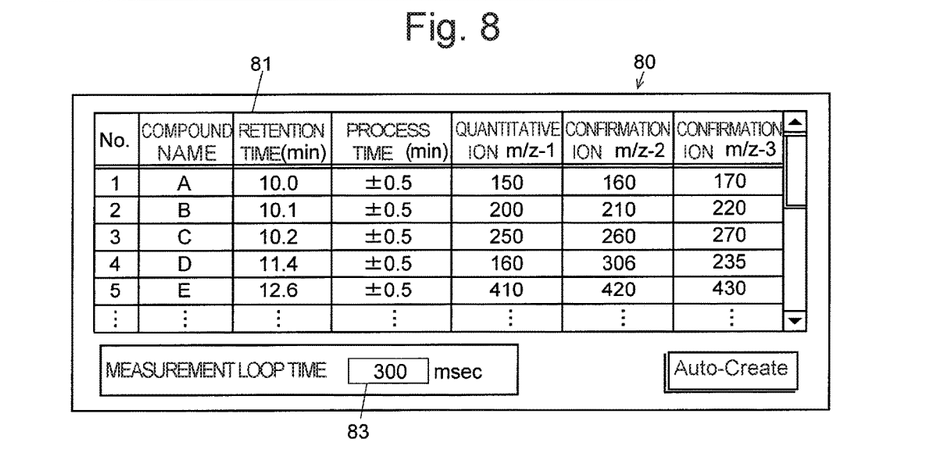
FIG. 8 is a diagram illustrating an example of a conventional settings input screen.

FIG. 8 illustrates an example of a settings input screen for allowing an analysis operator to set measurement conditions. As shown in the figure, a compound table display field 81 in which a compound table is displayed, and a measurement loop time input field 83 for allowing an analysis operator to input a setting value for a measurement point time interval, which is called a measurement loop time, are provided on the settings input screen 80.

Figure 9:
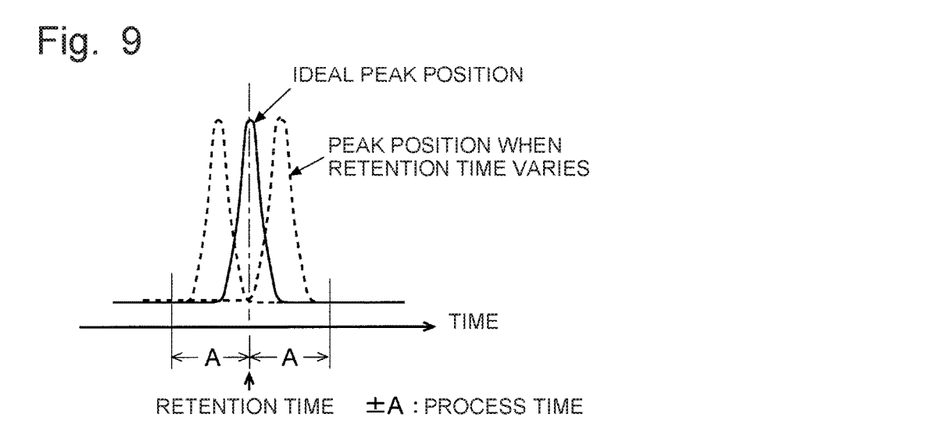
FIG. 9 is a diagram illustrating the relationship between the peak of a compound on a chromatogram and a retention time and process time.

The compound table displayed in the compound table display field 81 includes information of a compound name, a predicted retention time, a process time, a mass-to-charge ratio of a quantitative ion, and a mass-to-charge ratio of a confirmation ion for each target compound. The quantitative ion is an ion which best characterizes the compound. The confirmation ion is an ion which has a mass-to-charge ratio different from that of the quantitative ion and characterizes the compound. This confirmation ion is typically used to confirm that the chromatogram peak of the quantitative ion originates from the target compound by using the relative ratio between the signal intensity of the confirmation ion peak and the signal intensity of the quantitative ion peak on the mass spectrum. The retention time is a predicted value of the time of elution from a column in the liquid chromatograph. The process time is a parameter for designating a time range centering the predicted retention time during which the compound is to be measured, where an appropriate time margin is set so as to accommodate the variation in peak width and retention time. Accordingly, even if the retention time of a certain compound varies, the peak of the compound reliably appears within a range of the retention time of the compound±the process time. FIG. 9 shows the relationship between the peak of a compound on a chromatogram and the retention time and process time.

In the process of automatically creating the parameter table, a measurement time is appropriately divided into segments based on the compound table as described above. A segment is the smallest time unit for setting measurement conditions such as the conditions regarding the ions to be measured. The measurement conditions can be switched on a segment-by-segment basis.

In the process of automatically creating a parameter table, a boundary between segments is automatically set at a time point within an interval between retention times of compounds to be measured which is sufficiently large. More specifically, if a conditional expression, ([the retention time of a compound $X$]+[$A$])<([the retention time of the compound $X$+1 eluted next after the compound $X$]−[$A$]) (where ±$A$ is a process time)  (1)

is satisfied, the segment boundary is set at a time point where the elution time range (retention time±$A$) of the compound X does not overlap the elution time range of the compound X+1, typically an intermediate time point between the retention time for the compound X and the retention time for the compound X+1, and thus the measurement time is divided into a plurality of segments by the segment boundary.

Figure 10A:
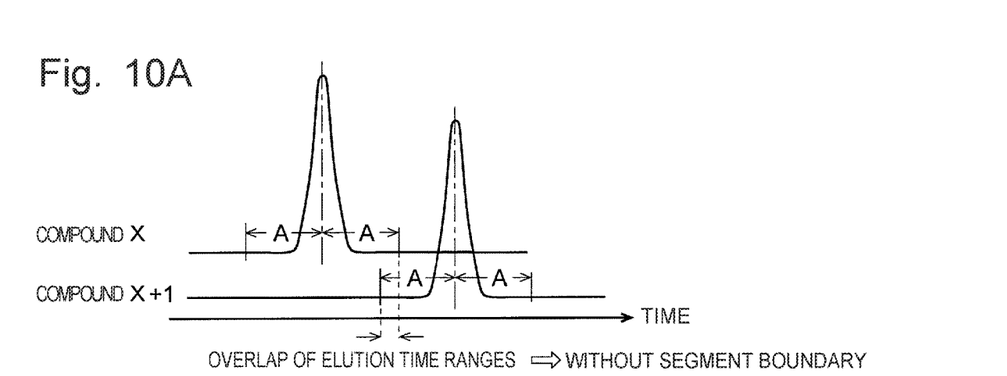
FIG. 10A and FIG. 10B are diagrams illustrating a chromatogram for describing a conventional segment dividing method.
Figure 10B:
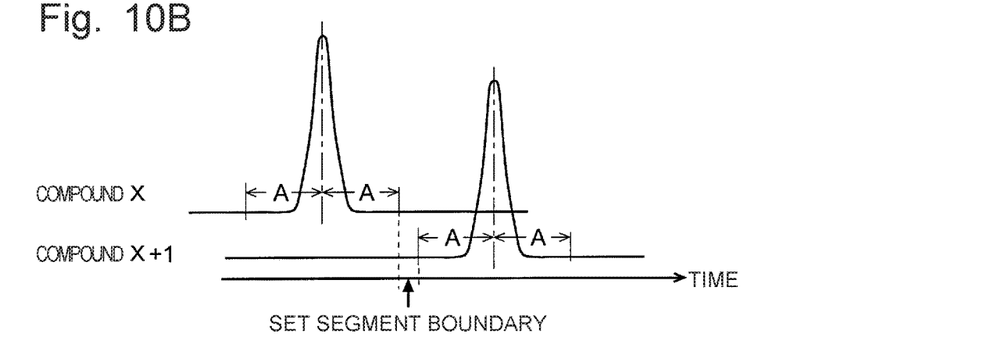

FIG. 10A and FIG. 10B show chromatograms for describing a segment dividing method. As shown in FIG. 10A, if the elution time ranges of the compound X and the compound X+1 overlap with each other, no segment boundary is set. That is to say, in this case, the compound X and the compound X+1 belong to the same segment. On the other hand, as shown in FIG. 10B, if the elution time ranges of the compound X and the compound X+1 do not overlap with each other, a segment boundary is determined at an intermediate point between the retention time of the compound X and the retention time of the compound X+1. Therefore, the compound X and the compound X+1 belong to different segments. According to such an algorithm, segments can be defined for all the compounds (or some compounds which are designated by an analysis operator) listed in the compound table.

Figure 11:
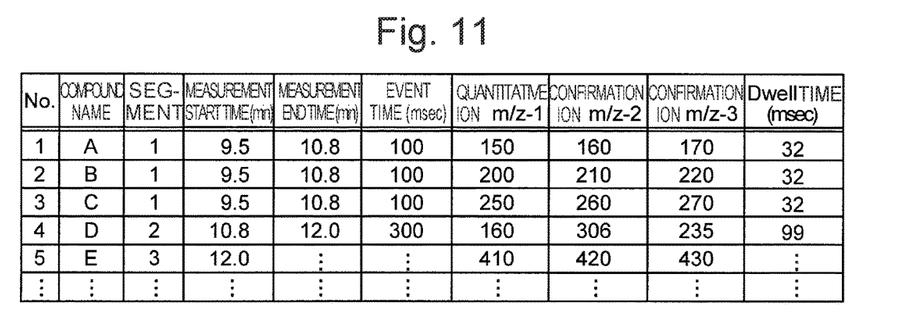
FIG. 11 is a diagram illustrating a parameter table created by a conventional automatic parameter table creation function based on the compound table shown in FIG. 8.

FIG. 11 shows one example of a parameter table that is automatically created based on the compound table shown in FIG. 8. In the parameter table, the measurement conditions for one compound are listed together on one row, with each row including, besides the compound name, the number of a segment where the compound is measured (hereinafter, the segment number is indicated by "#"), the measurement start time, the measurement end time, the event time, the mass-to-charge ratios of the ions to be measured, and the dwell time. For the mass-to-charge ratios of the ion to be measured, the mass-to-charge ratio m/z–1 of the quantitative ion as well as the mass-to-charge ratios of the confirmation ions m/z–2 and m/z–3 of the compound to be measured are set. The measurement start time and the measurement end time are the start time and the end time of the segment in question. The event time is the time allotted to perform measurement once (this is called a "measurement event") for one compound. The dwell time is the time during which the detector actually receives and accumulates ions, that is, the data collection time.

Figure 12:
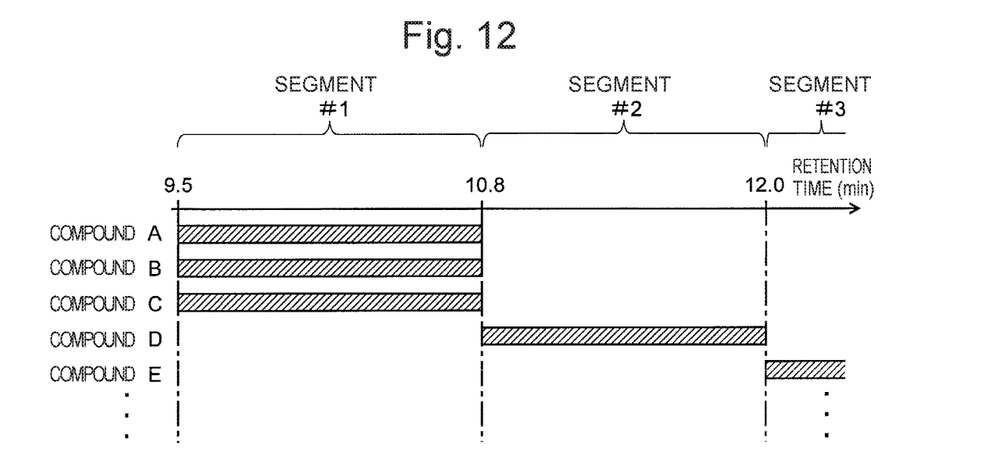
FIG. 12 is a schematic diagram showing the correspondence between compounds and segments created based on the compound table shown in FIG. 8.

In the example in FIG. 8 and FIG. 11, a time interval sufficiently satisfying the conditional expression (1) exists between a compound C and a compound D subsequently eluting from the column. Accordingly, a segment boundary is set there. Segment #1 and segment #2 are created before and after the boundary, respectively. Further, since a time interval sufficiently satisfying the conditional expression (1) exists between the compound D and a subsequently eluting compound E, a segment boundary is also set there, and segment #3 is created after the boundary. Thus, compounds A to C are assigned to be measured in the time period of segment #1 whose measurement start time is 9.5 [min] and measurement end time is 10.8 [min], and the compound D is assigned to be measured in the time period of segment #2 whose measurement start time is 10.8 [min] and measurement end time is 12.0 [min]. FIG. 12 is a schematic diagram showing the correspondence between segments and compounds shown in FIG. 11, with time as the abscissa.

The event time is automatically calculated based on the setting value of the measurement loop time that the analysis operator input to the measurement loop time input field 83 of the settings input screen 80 and the number of compounds measured in one segment. FIG. 11 shows an example where the measurement loop time is set to 300 [msec]. In this case, the ions originating from each compound need to be measured at an interval of a measurement loop time of 300 [msec]. Since the compounds to be measured in segment #1 are the three kinds of compounds A to C, the event time allotted to each compound is 300 [msec]÷3=100 [msec]. In segment #2, the compound to be measured is the compound D alone, and hence 300 [msec] that is the same as the measurement loop time is allotted as the event time.

As described above, the dwell time is the time during which the detector actually captures ions. The event time includes, in addition to the dwell time, a wait time (hereinafter, called "voltage stabilization wait time") which is required for the voltage to stabilize after the voltage applied to a quadrupole mass filter is changed. The dwell time also depends on the number of ions to be measured (number of measurement target ions) in one event time. Accordingly, the dwell time $T_D$ for each ion is calculated by the following equation (2).

$$T_D=([\text{event time } T_I]-[\text{voltage stabilization wait time}])/[\text{number of ions to be measured}] \quad (2)$$

In the example illustrated in FIG. 11, the voltage stabilization wait time per ion to be measured is set to 1 [msec]. As a result, in segment #1, the dwell time $T_D$ for each ion is $(100-1\times3)\div3\approx32$ [msec]. Further, in segment #2, the dwell time $T_D$ for each ion is $(300-1\times3)\div3=99$ [msec].

CITATION LIST

Patent Literature

[Patent Literature 1] JP 2003-172726 A
[Patent Literature 2] JP 2012-132799 A

SUMMARY OF INVENTION

Technical Problem

The aforementioned dwell time influences the measurement sensitivity (SN ratio) and reproducibility of the peak area. Specifically, if the dwell time is too short, unfavorable effects of external factors, such as drift and noise, tend to be included in signal intensity data acquired by the detector, making it difficult to achieve sufficient measurement reproducibility. Accordingly, accurate quantitative determination requires a dwell time of an adequate length. However, as described above, ions originating from each compound must be measured in the respective measurement time intervals that are determined according to the measurement loop time. Therefore, if a large number of compounds are assigned to a single segment, the measurement time (the aforementioned event time) allotted to a single compound will be short, and consequently the dwell time will also be shortened.

In this connection, during actual measurement, there are cases where the sensitivity for only a specific compound among a plurality of compounds that are measured simultaneously is poor, and favorable sensitivity is obtained for the other compounds. In such a case, it is desirable to lengthen the dwell time for only the compound for which the sensitivity is poor to perform high-sensitivity analysis. However, in the conventional process for automatically creating a parameter table, as described above, the event time is determined by evenly dividing the measurement loop time by the number of compounds, and furthermore the dwell time is determined by evenly allocating the event time for each ion to be measured (measurement target ion) with respect to each compound, and hence it is not easy to lengthen the dwell time for only a specific compound. For example, if the event time of the compound in question is simply lengthened, the measurement loop time will no longer satisfy the requirement for the desired time period. Although it is also possible to adjust the event time of other compounds so as to satisfy the desired measurement loop time, such work will be extremely complicated and require a lot of time and labor if a large number of compounds need to be measured.

There are also cases where the sensitivity for only a specific ion originating from a specific compound is poor, and favorable sensitivity is obtained for the other ions. In such a case, although it is desirable to lengthen the dwell time for only the ion for which the sensitivity is poor and thereby perform high-sensitivity analysis, in this case also, similarly to the situation described above, it is not easy to adjust the dwell time so as to satisfy the desired measurement loop time.

The present invention was conceived in order to solve the problems described above, and a first object of the present invention is to provide a chromatograph mass spectrometer including an automatic parameter table creation function with which a setting can easily be made so as to perform a high-sensitivity analysis with respect to only some compounds among a plurality of compounds as measurement objects. A second object of the present invention is to provide a chromatograph mass spectrometer including an automatic parameter table creation function with which a setting can easily be made so as to perform a high-sensitivity analysis with respect to only some ions among a plurality of ions to be measured with regard to a compound that is a measurement object.

Solution to Problem

A chromatograph mass spectrometer according to a first invention that was conceived to solve the problems described above is a chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:

a) compound table holding means for storing a compound table including at least information identifying, for each compound to be measured, an elution time range and mass-to-charge ratios of one or more ions to be measured;

b) high-sensitivity analysis designation acceptance means for allowing an analysis operator to designate whether or not to perform a high-sensitivity analysis with respect to each of the compounds included in the compound table;

c) segment setting means for determining a boundary at a time point where the elution time ranges of the compounds included in the compound table do not overlap with each other to set segments each of which is a measurement time unit, and assigning one or more compounds to be measured to each of the segments;

d) event time determination means for, for each of the segments set by the segment setting means, determining an event time, which is a measurement time for each compound, by dividing a measurement loop time, which is a previously given measurement point time interval for each ion, according to a number of compounds assigned to the pertinent segment; and e) dwell time determination means for determining a dwell time, which is a data collection time for each mass-to-charge ratio, based on the event time determined by the event time determination means and a number of ions to be measured for each compound;

wherein, in a case where a compound that is an object of the high-sensitivity analysis is included among the compounds assigned to the pertinent segment, the event time determination means divides the measurement loop time so that a ratio of an event time of the compound that is the object of the high-sensitivity analysis to an event time of other compounds assigned to the same segment is a predetermined ratio.

According to the chromatograph mass spectrometer of the first invention having the above described configuration, an analysis operator, by simply using the high-sensitivity analysis designation acceptance means to designate a compound or compounds as an object of a high-sensitivity analysis, can make a setting so as to lengthen the event time of the compound or compounds by a predetermined ratio relative to the event time of other compounds assigned to the same segment without changing the measurement loop time. By lengthening the event time, the dwell times for one or more ions to be measured with respect to the pertinent compound or compounds is also lengthened, and hence the measurement sensitivity for the compound or compounds can be improved.

A chromatograph mass spectrometer according to a second invention that was conceived to solve the problems described above is a chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:

a) compound table holding means for storing a compound table including at least information identifying, for each compound to be measured, an elution time range and mass-to-charge ratios of one or more ions to be measured;

b) high-sensitivity analysis designation acceptance means for allowing an analysis operator to designate whether or not to perform a high-sensitivity analysis with respect to each of the mass-to-charge ratios included in the compound table;

c) segment setting means for determining a boundary at a time point where the elution time ranges of the compounds included in the compound table do not overlap with each other to set segments each of which is a measurement time unit, and assigning one or more compounds to be measured to each of the segments;

d) event time determination means for, for each of the segments set by the segment setting means, determining an event time, which is a measurement time for each compound, based on a measurement loop time, which is a previously given measurement point time interval for each ion, and a number of compounds assigned to the pertinent segment; and e) dwell time determination means for determining a dwell time, which is a data collection time for each mass-to-charge ratio, by dividing the event time determined for each of the compounds by the event time determination means, according to a number of mass-to-charge ratios to be measured for a compound corresponding to the event time;

wherein, in a case where a mass-to-charge ratio that is designated as an object of the high-sensitivity analysis is included in the mass-to-charge ratios to be measured for the compound corresponding to the event time, the dwell time determination means divides the event time so that a ratio of a dwell time of the mass-to-charge ratio that is designated as the object of the high-sensitivity analysis to a dwell time of other mass-to-charge ratios to be measured with respect to the same compound is a previously given ratio.

According to the chromatograph mass spectrometer of the second invention having the above described configuration, an analysis operator, by simply using the high-sensitivity analysis designation acceptance means to designate a mass-to-charge ratio or mass-to-charge ratios as an object of a high-sensitivity analysis, can make a setting so as to lengthen the dwell times of the mass-to-charge ratio or mass-to-charge ratios by a predetermined ratio relative to the dwell time of other mass-to-charge ratios to be measured with respect to the same compound without automatically changing the measurement loop time and event time.

A chromatograph mass spectrometer according to a third invention that was conceived to solve the problems described above is a chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:

a) compound table holding means for storing a compound table including at least information identifying, for each compound to be measured, an elution time range, a mass-to-charge ratio of a quantitative ion to be measured, and a mass-to-charge ratio of a confirmation ion to be measured;

b) high-sensitivity analysis designation acceptance means for allowing an analysis operator to designate whether or not to perform a high-sensitivity analysis with respect to each of the compounds included in the compound table;

c) segment setting means for determining a boundary at a time point where the elution time ranges of the compounds included in the compound table do not overlap with each other to set segments each of which is a measurement time unit, and assigning one or more compounds to be measured to each of the segments;

d) event time determination means for, for each of the segments set by the segment setting means, determining an event time, which is a measurement time for each compound, based on a measurement loop time, which is a previously given measurement point time interval for each ion, and a number of compounds assigned to the pertinent segment; and e) dwell time determination means for determining a dwell time, which is a data collection time for each mass-to-charge ratio, by dividing the event time determined for each of the compounds by the event time determination means, according to a number of mass-to-charge ratios to be measured for a compound corresponding to the event time;

wherein, in a case where the compound corresponding to the event time is designated as an object of the high-sensitivity analysis, the dwell time determination means divides the event time so that a ratio of a dwell time of a mass-to-charge ratio of a quantitative ion to be measured with respect to the compound to a dwell time of a mass-to-charge ratio of a confirmation ion to be measured with respect to the compound becomes a previously given ratio.

According to the chromatograph mass spectrometer of the third invention having the above described configuration, if an analysis operator designates any compound from among measurement target compounds using the high-sensitivity analysis designation acceptance means, the mass-to-charge ratio of a quantitative ion to be measured with respect to the designated compound is automatically designated as an object of the high-sensitivity analysis. Further, without changing the measurement loop time and the event time, a dwell time relating to the mass-to-charge ratio of the quantitative ion of the compound can be lengthened by a predetermined ratio relative to a dwell time relating to the mass-to-charge ratio of a confirmation ion of the same compound.

In the above described first invention, second invention and third invention, the "elution time range" of a compound is a time range set so as to secure a prescribed time width (that is, the aforementioned "process time") that is defined in consideration of the peak width and positional variations of the peak around the predicted retention time of the compound. The time width changes depending on the extent to which a margin is taken into account. Accordingly, the time width may be previously defined as a default, or alternatively, an analysis operator may be allowed to input and set the time width. In the above described compound table, the value of the elution time range itself may be described as the "information identifying" the elution time range, or alternatively, for example, the predicted retention time and the time width may be described, or only the predicted retention time may be described. If the predicted retention time and the time width are determined, the elution time range can be uniquely determined. Further, in a case where only the retention times are defined in association with respective compounds in the compound table, the elution time ranges of the respective compounds can be calculated based on the retention times and default or externally designated time widths.

The "measurement loop time, which is a previously given measurement point time interval for each ion," and the "predetermined ratio" may also be defined in advance as defaults. Alternatively, the analysis operator may be allowed to input and set these items.

Advantageous Effects of Invention

As described above, according to the chromatograph mass spectrometer of the first invention, in a chromatograph mass spectrometer including an automatic parameter table creation function, by performing a simple operation it is possible to make a setting to perform a high-sensitivity analysis on only some compounds among a plurality of compounds that are measurement targets. Further, according to the chromatograph mass spectrometer of the second invention or third invention, in a chromatograph mass spectrometer including an automatic parameter table creation function, by performing a simple operation it is possible to make a setting to perform a high-sensitivity analysis on only some ions among a plurality of ions to be measured for respective compounds.

DESCRIPTION OF EMBODIMENTS

Modes for implementing the present invention will now be described by way of embodiments.

Embodiment 1

Figure 1:
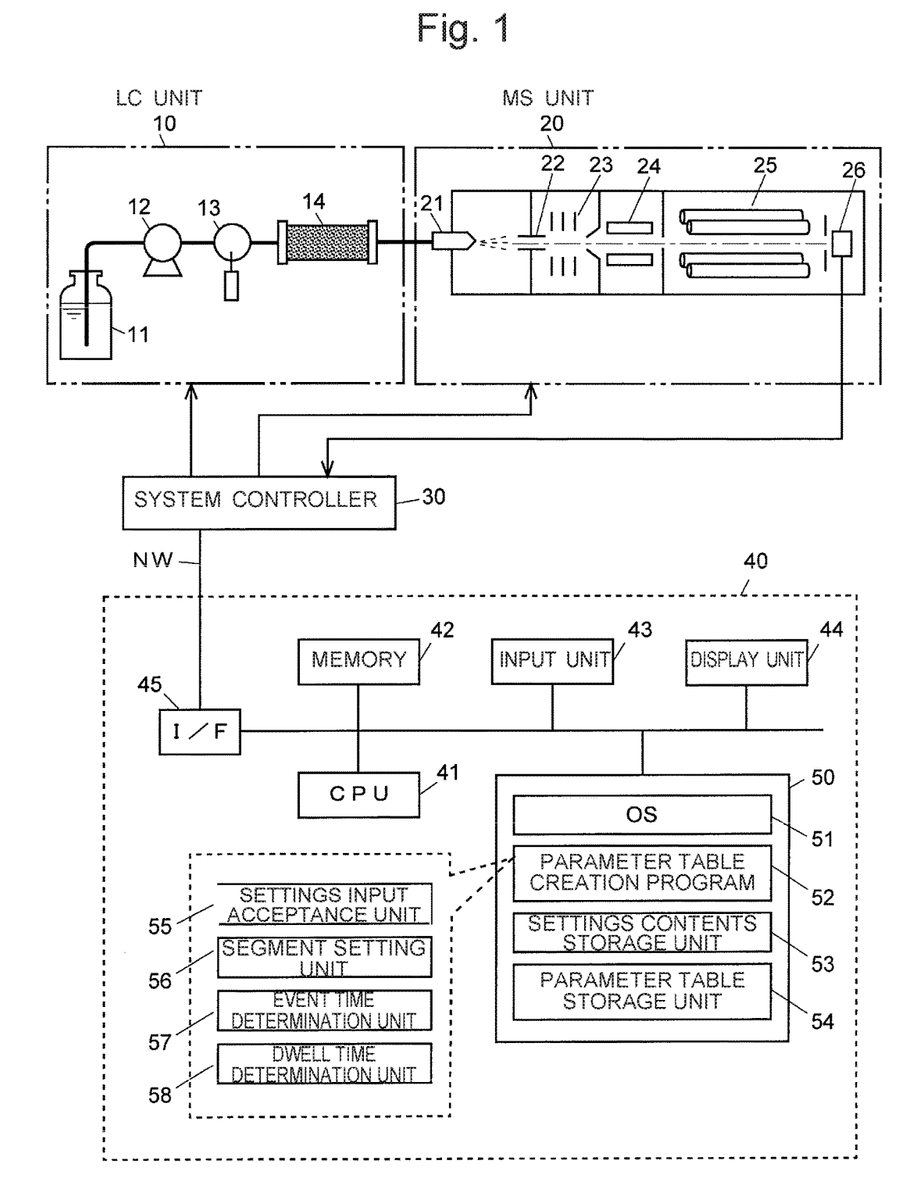
FIG. 1 is a configuration diagram of a main part of an LC-MS as a first embodiment of the present invention.

FIG. 1 is a configuration diagram of a main part of an LC-MS according to a first embodiment. The LC-MS of the present embodiment includes a liquid chromatograph unit (LC unit) 10 for separating various compounds contained in a sample in the temporal direction, a mass spectrometer unit (MS unit) 20 for performing mass spectrometric analysis of the separated various compounds, a system controller 30 connected to the LC unit 10 and the MS unit 20, and a control/processing unit 40 for controlling the LC unit 10 and the MS unit 20 and processing data output from the MS unit 20, through the system controller 30.

The LC unit 10 includes a mobile phase container 11 for storing a mobile phase, a liquid transport pump 12 for sucking the mobile phase and transporting it at a constant flow rate, an injector 13 for injecting a sample into the mobile phase at a predetermined timing, and a column 14 for temporally separating various compounds in the sample.

The MS unit 20 includes a spray nozzle 21 for ionizing an eluate containing compounds eluted from the column 14 by electrospraying the eluate into an atmospheric environment, a heating capillary 22 for guiding the ions originating from the compounds in the sample into a vacuum environment, ion guides 23 and 24 for transporting the ions to the subsequent stage while focusing the ions, a quadrupole mass filter 25 for allowing only ions having a specific mass-to-charge ratio to pass, and a detector 26 for detecting the ions that passed through the quadrupole mass filter 25.

A detection signal obtained by the detector 26 of the MS unit 20 is converted into digital values by an A/D converter, not shown, and subsequently input into the control/processing unit 40 via the system controller 30. The control/processing unit 40 creates a mass spectrum and a chromatogram and performs quantitative analysis by executing a prescribed operation process. The control/processing unit 40 is physically embodied by a computer such as a personal computer. In the control/processing unit 40, a CPU (central processing unit) 41, a memory 42, an input unit 43 constituted by a keyboard or a mouse or the like, a display unit 44 constituted by an LCD (liquid crystal display) or the like, and a storage unit 50 constituted by a mass storage device such as a hard disk or an SSD (solid state drive) are connected to each other. An OS (operating system) 51 and a parameter table creation program 52 (program according to the present invention) are stored in the storage unit 50. In addition, a settings contents storage unit 53 (corresponds to a compound table holding unit in the present invention) and a parameter table storage unit 54 are provided in the storage unit 50. The control/processing unit 40 also includes an interface (I/F) 45 for controlling a direct connection with an external device or a connection via a network such as an LAN (local area network) with an external device or the like, and is connected to the system controller 30 through a network cable NW (or a wireless LAN) by the interface 45.

In FIG. 1, a settings input acceptance unit 55, a segment setting unit 56, an event time determination unit 57 and a dwell time determination unit 58 are illustrated so as to relate to the parameter table creation program 52. Each of these units is functional means that is fundamentally realized by software by execution of the parameter table creation program 52 by the CPU 41. In this connection, the parameter table creation program 52 need not necessarily be a stand-alone program, and for example may be a function that is incorporated into a part of a program for controlling the LC unit 10 and the MS unit 20, and there are no specific limitations as to the form thereof.

An example of performing quantitative analysis of a known compound contained in a sample using the LC-MS of the present embodiment will be briefly described. In this case, the quadrupole mass filter 25 of the MS unit 20 is driven in an SIM measurement mode so as to selectively allow ions with specific mass-to-charge ratios originating from a compound to be quantitatively analyzed (hereinafter referred to as "target compound") to pass therethrough.

In a state where the mobile phase is being transported by the liquid transport pump 12 into the column 14 at a substantially constant flow rate, the injector 13 injects the sample into the mobile phase. The injected sample is carried by the mobile phase and introduced into the column 14, and various compounds in the sample are temporally separated while passing through the column 14. At around a time point after a prescribed time that is based on the sample injected time point elapses (that is, in proximity to the retention time of a target compound), the target compound is eluted from an outlet of the column 14, and the target compound reaches the spray nozzle 21 of the MS unit 20, and ions are generated that originate from the compound. The ions pass through the heating capillary 22 and the ion guides 23 and 24, and are introduced into the quadrupole mass filter 25. The quadrupole mass filter 25 allows only ions having specific mass-to-charge ratios that are originating from the target compound to selectively pass therethrough. The ions passed through the quadrupole mass filter 25 reach the detector 26 and are detected. The control/processing unit 40 creates a mass chromatogram (also called an "extracted ion chromatogram") which shows the relationship between ion intensities at the aforementioned specific mass-to-charge ratios and the passage of time, according to data based on detection signals obtained from the detector 26.

If the sample contains the target compound, a peak appears in the vicinity of the retention time of the target compound on the mass chromatogram. Therefore, the control/processing unit 40 extracts the peak originating from the target compound on the mass chromatogram, and calculates the peak area value. The control/processing unit 40 refers to a calibration curve which indicates the relationship between peak area values and the concentration (the content) of the target compound that is previously created according to results acquired by measuring a standard sample and the like, to thereby calculate the concentration of the target compound. If there is a plurality of compounds to be quantitatively analyzed, a mass chromatogram is created based on data obtained by performing SIM measurement with respect to mass-to-charge ratios that differ for each compound, the area values of the peaks originating from the respective target compounds are calculated as described above, and the concentration of the pertinent compound is calculated based on the area value.

In the LC-MS of the present embodiment, the control/processing unit 40 controls the operations of the LC unit 10 and the MS unit 20 according to the parameter table stored in the parameter table storage unit 54 of the storage unit 50. In the case of quantitating a large number of compounds contained in a sample with a single sample injection such as, in particular, in the case of multi-component simultaneous analysis, creation of a parameter table by the analysis operator himself/herself is significantly complicated and errors are liable to occur. Therefore, the control/processing unit 40 includes the parameter table creation program 52 which automatically creates a parameter table based on a compound table, and the parameter table creation program 52 has characteristic functions that are different from those of the conventional automatic parameter table creation.

Figure 2:
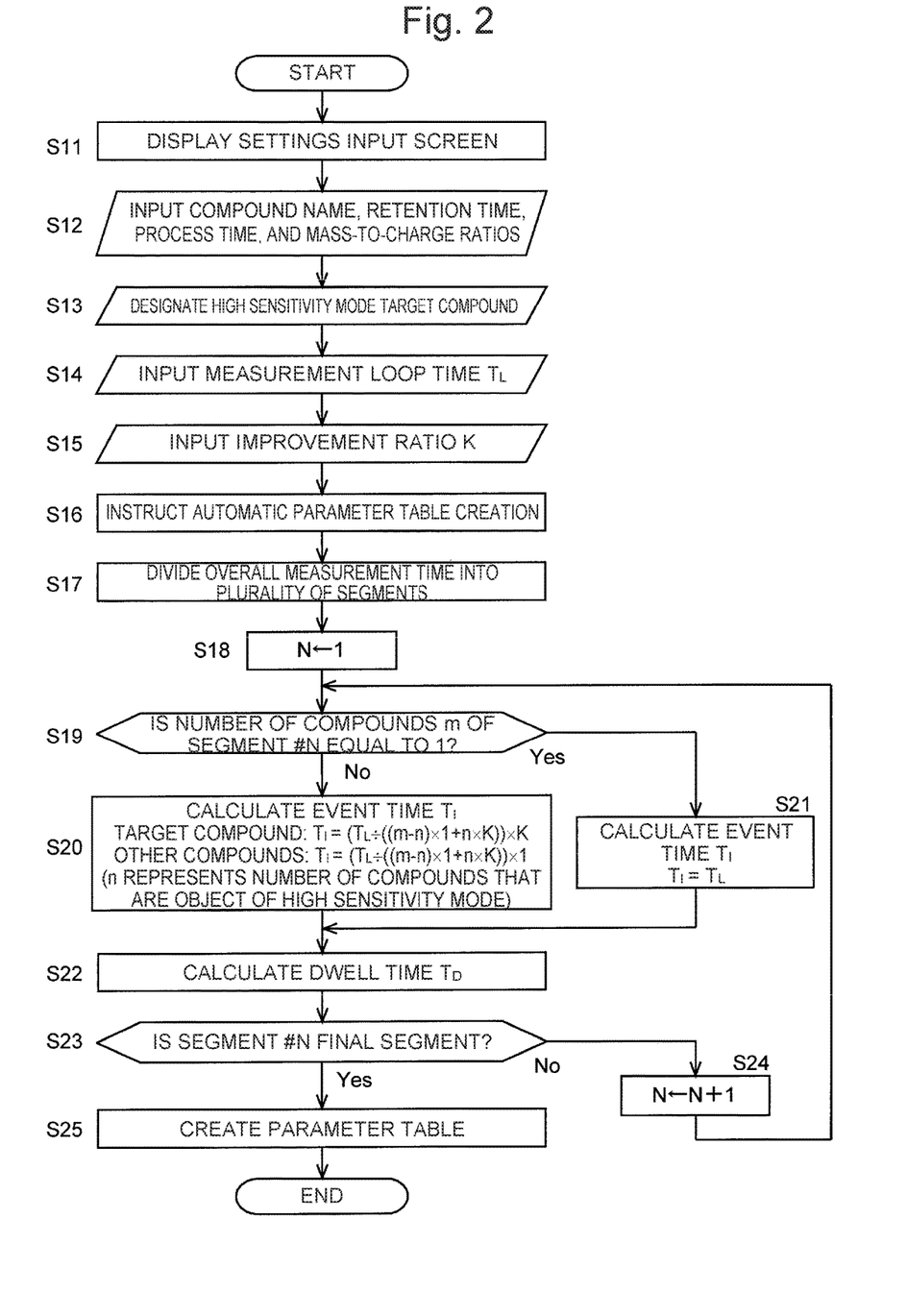
FIG. 2 is a flowchart of operations when executing an automatic parameter table creation process in the LC-MS of the first embodiment.

Hereunder, a characteristic parameter table creation process that is executed mainly using the parameter table creation program 52 will be described in detail. FIG. 2 is a flowchart of parameter table creation processing in the LC-MS of the present embodiment.

Figure 3:
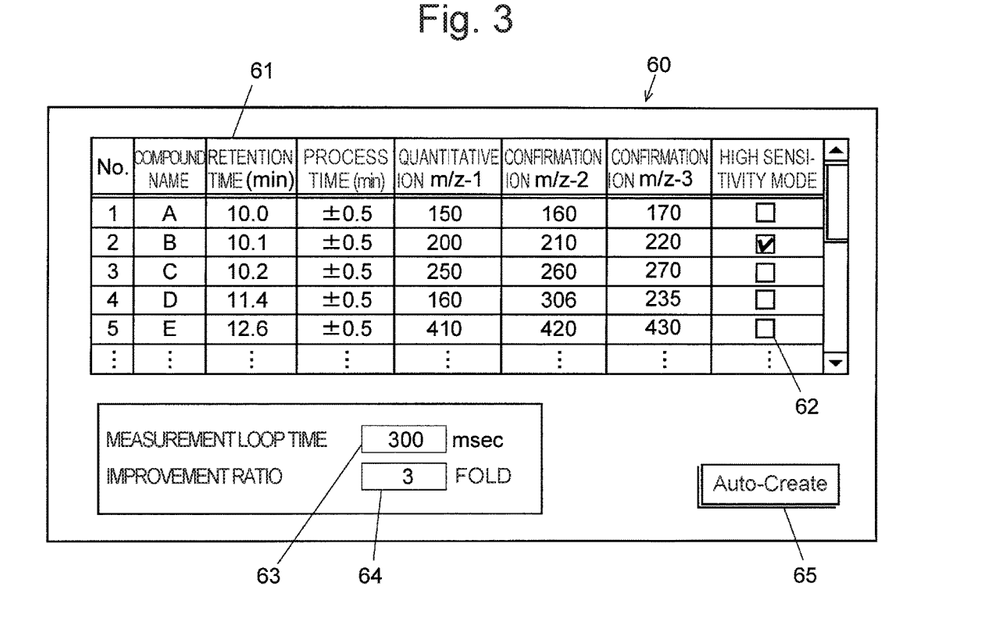
FIG. 3 is a diagram illustrating an example of a settings input screen on the LC-MS of the first embodiment.

First, when the analysis operator starts the parameter table creation program 52 by performing a predetermined operation using the input unit 43, the settings input acceptance unit 55 displays a settings input screen 60 as illustrated in FIG. 3 on the screen of the display unit 44 (step S11). A compound table display field 61 in which a compound table that is the object for creation of a parameter table is displayed, a measurement loop time input field 63 and an improvement ratio input field 64 are provided on the settings input screen 60. In the compound table displayed in the compound table display field 61, one row corresponds to a single compound, and for each of a plurality of compounds to be measured, it is possible to set the compound name, retention time, process time, and a single mass-to-charge ratio of a quantitative ion (m/z–1) and two mass-to-charge ratios of confirmation ions (m/z–2, m/z–3) to be measured with respect to the compound in question. In addition, in each row of the compound table, as a characteristic element of the present embodiment, a check box 62 is provided for designating whether or not the compounds corresponding to the respective rows are to be taken as an object of a high sensitivity mode.

The analysis operator inputs the compound name, retention time, process time and mass-to-charge ratios (m/z–1, m/z–2 and m/z–3) of each target compound in the compound table through the input unit 43 (step S12). In the example illustrated in FIG. 3, the same contents as in the compound table illustrated in FIG. 8 are input for these items. The analysis operator also checks the check box 62 of compounds that are to be taken as an object of the high sensitivity mode among the target compounds that were input to the compound table (step S13), and then inputs appropriate numerical values in the measurement loop time input field 63 and the improvement ratio input field 64, respectively (steps S14 and S15). In the example in FIG. 3, a compound B is selected as a compound to be taken as an object of the high sensitivity mode, the measurement loop time $T_L$ is set to 300 [msec], and an improvement ratio K is set to 3 [-fold]. In this case, the term "improvement ratio" refers to a ratio between the event time of the compound that is the object of the high sensitivity mode and the event time of the other compounds among the plurality of compounds belonging to the same segment, and means that, for example, when the improvement ratio K is "3", the event time for a compound that is an object of the high sensitivity mode will be three times longer than the event time for the other compounds.

When the analysis operator clicks on an "Auto-Create" button 65 in a state in which the above described input of settings has been completed, the contents that were set on the settings input screen 60 are stored in the settings contents storage unit 53, and an instruction is issued to execute a process to automatically create a parameter table (step S16). Upon receiving the instruction, the segment setting unit 56 reads the compound table from the settings contents storage unit 53, and sets segments in which the entire measurement time or a part thereof is appropriately divided in a manner similar to that of the conventional method, based on the retention time and the set process time for each of the compounds listed in the compound table (step S17). More specifically, two compounds having adjacent retention times which satisfy the conditional expression represented by the above described expression (1) are retrieved, and the time is separated by taking an intermediate point between the retention times of the two compounds as the segment boundary. In the compound table illustrated in FIG. 3, since the two compounds C and D satisfy the conditional expression (1), a segment boundary is set at 10.8 (min) that is the intermediate point between the retention times of the compounds C and D, and a segment before the boundary is referred to as "segment #1" and a segment after the boundary is referred to as "segment #2". Further, since the compounds D and E also satisfy the conditional expression (1), a segment boundary is also set at 12.0 (min) that is the intermediate point between the retention times of the compounds D and E, and a segment after the boundary is referred to as "segment #3". As a result, all of the compounds A to C are assigned so as to be measured during the period of segment #1 whose measurement start time is 9.5 [min] and measurement end time is 10.8 [min], and the compound D is assigned so as to be measured during the period of segment #2 whose measurement start time is 10.8 [min] and measurement end time is 12.0 [min]. The relationship between the segments and compounds at this time is as shown in aforementioned FIG. 12.

Next, the parameter table creation program 52 sets a variable N to 1 (step S18), and determines whether or not a number of compounds m assigned to a segment #N that was set in step S17 is equal to 1 (step S19). If m is not 1, that is, if a plurality of compounds were assigned to the segment #N, the parameter table creation program 52 proceeds to step S20 to calculate event times.

The method for calculating event times in step S20 will now be described. In a single segment, measurement relating to one or more compounds assigned to the segment in question is repeatedly executed. The length of the execution time for each repeated measurement is a measurement loop time $T_L$. An event time $T_I$ which is the time taken for measurement per compound during one measurement among the repeated measurements is determined by dividing the measurement loop time $T_L$ according to the number of compounds assigned to the segment. In the conventional automatic parameter table creation method, the event time $T_I$ is determined by evenly dividing the measurement loop time $T_L$ by the number of compounds m assigned to the same segment, and consequently the event times of a plurality of compounds assigned to a single segment have been identical to each other. In this respect, in the LC-MS according to the present embodiment, the measurement loop time $T_L$ is divided so that the event time for a compound that is an object of the high sensitivity mode is a time obtained by multiplying the event time for the other compounds by a multiple of K (K is the improvement ratio). For example, in the case of the example in FIG. 3, as described above, the compounds A to C are assigned to segment #1, and among those the compound B is designated as an object of the high sensitivity mode. The measurement loop time $T_L$ is 300 [msec] and the improvement ratio K is 3 [-times]. Accordingly, the event time for the compound B is (300÷(1+1+3))×3=180 [msec], and the event time for each of the compounds A and B is (300÷(1+1+3))×1=60 [msec]. These expressions can be generalized as follows.

Event time of compound that is object of high sensitivity mode: $T_I = (T_L \div ((m-n) \times 1 + n \times K)) \times K$ Event time of other compounds: $T_I = (T_L \div ((m-n) \times 1 + n \times K)) \times 1$ (Where, m: number of compounds assigned to segment #N, n: number of compounds designated as object of high sensitivity mode among compounds assigned to segment #N).

On the other hand, if the number of compounds m assigned to the segment #N is 1 ("Yes" in step S19), regardless of whether or not the compound is an object of the high sensitivity mode, the event time determination unit 57 sets the event time $T_I$ to a value that is equal to the measurement loop time $T_L$ (step S21). For example, in the example illustrated in FIG. 3, since only one compound (compound D) is assigned to segment #2, the event time $T_I$ relating to the pertinent compound is 300 [msec], which is the same as the measurement loop time $T_L$.

In a case such as this in which only one compound is assigned to a single segment, because the event time will be the same irrespective of whether or not the pertinent compound is designated as an object of the high sensitivity mode, it is not possible to obtain the effect achieved by the high sensitivity mode. Therefore, in such a case, it is desirable to notify the analysis operator of such a fact using the display unit 44 or the like.

Next, the dwell time determination unit 58 calculates a dwell time (data accumulation time period) with respect to the mass-to-charge ratios of a plurality of ions to be measured for each target compound (step S22). In the example in FIG. 3, because there are three ions (quantitative ion m/z-1, confirmation ion m/z-2, and confirmation ion m/z-3) to be measured for a single compound, if it is assumed that the voltage stabilization wait time is 1 [msec], the dwell time $T_D$ for the respective ions of the compounds A and C belonging to segment #1 is (60−1×3)÷3=19 [msec], and the dwell time $T_D$ for the respective ions of compound B is (180−1×3)÷3=59 [msec]. Further, the dwell time $T_D$ for the respective ions of compound D belonging to segment #2 is (300−1×3)÷3=99 [msec].

In this connection, in step S20, if all of a plurality of compounds that are assigned to the same segment have been designated as objects of the high sensitivity mode, the event times for these compounds will all be equal, and it will not be possible to obtain the effect of the high sensitivity mode. Therefore, in such a case also, it is desirable to notify the analysis operator in a similar manner to the above described case.

Next, the parameter table creation program 52 determines whether or not the segment #N is the final segment (step S23). If the segment #N is not the final segment, the parameter table creation program 52 increments the variable N (step S24) and returns to step S19. Accordingly, processing is executed in time order for all of the segments that were set in step S17, and when the final segment is reached, the result determined in step S23 is "Yes". Thereupon, a parameter table that includes the event times and dwell times and the like calculated as described above is created (step S25), and is stored in the parameter table storage unit 54.

Figure 4:
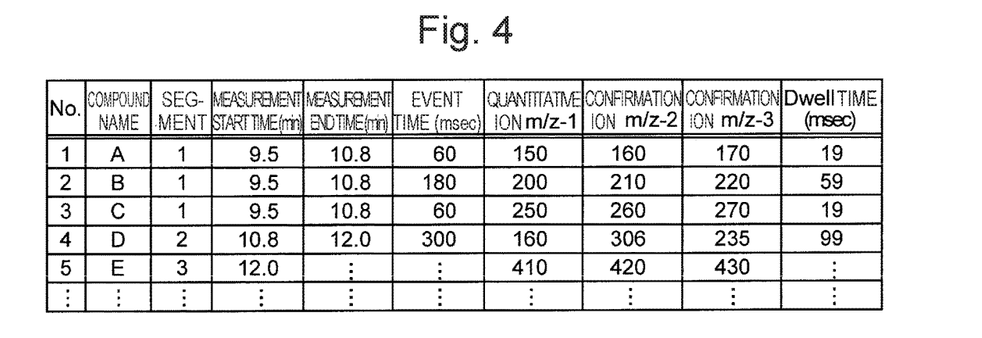
FIG. 4 is a diagram illustrating a parameter table created by executing an automatic parameter table creation process in the LC-MS of the first embodiment based on setting contents that are set using the settings input screen shown in FIG. 3.

FIG. 4 is an example of a parameter table that is automatically created based on the contents of the settings input screen shown in FIG. 3. As will be understood from the example illustrated in FIG. 4, among the compounds A to C assigned to segment #1, the event time and dwell time for compound B that is a compound that is an object of the high sensitivity mode are longer than the event time and dwell time of the other compounds (compounds A and C). In the example in FIG. 4, the total event time for the compounds A to C is 60+180+60=300 [msec], which is equal to the measurement loop time $T_L$ set in step S14. Further, the ratio of the event time for compound B relative to the event time for compounds A and C is 180÷60=3, which is equal to the improvement ratio K set in step S15. Thus, according to the LC-MS of the present embodiment, by merely perform a simple operation to designate compounds to be objects of the high sensitivity mode and also input an improvement ratio on the settings input screen 60, the analysis operator can set the event time of the designated compounds a longer time than the event time of the other compounds without affecting the measurement loop time.

The parameter table creation program 52 according to the present embodiment can exert a more excellent effect when performing multicomponent simultaneous analysis. In a case of simultaneously analyzing a large number of components contained in a sample, because the number of compounds that are eluted temporally adjacent to each other from the LC unit 10 increases, the number of compounds belonging to the same segment increases. A case will now be considered in which, in the process for automatically creating a parameter table for such kind of multicomponent simultaneous analysis, 10 kinds of compounds, referred to as compounds A to J, among a large number of compounds contained in a sample are assigned to the same segment, and a compound B among the compounds A to J is designated as a compound that is an object of the high sensitivity mode. At this time, for compound B that is the object of the high sensitivity mode, the event time is (300÷(1×9+3×1))×3=75 [msec] and the dwell time is (75−1×3)÷3=24 [msec]. For the other compounds (compounds A and C to J), the event time is (300÷(1×9+3×1))×1=25 [msec] and the dwell time is (25−1×3)÷3≈7.3 [msec]. On the other hand, according to the conventional process for automatically creating a parameter table, the event time for each of these compounds is 300÷10=30 [msec], and the dwell time is (30−1×3)÷3=9 [msec]. Thus, according to the parameter table creation program 52 of the present embodiment, the dwell time of a compound that is the object of the high sensitivity mode is a multiple of 24÷9≈2.7 relative to the dwell time obtained with the conventional method, and the dwell time of the other compounds is a multiple of 7.3÷9≈0.81 relative to the dwell time obtained with the conventional method. Therefore, for a compound that is the object of the high sensitivity mode, the SN ratio is also a high sensitivity that is a multiple of 2.7 relative to the SN ratio obtained with the conventional method, and even for the other compounds, a decrease in the SN ratio is suppressed to a minimum that is a value that is a multiple of approximately 0.8 relative to the SN ratio obtained with the conventional method. This is because the demerit (that is, a decrease in the dwell time for other compounds) that arises due to measuring some compounds in the high sensitivity mode is spread among a large number of compounds.

Embodiment 2

Figure 5:
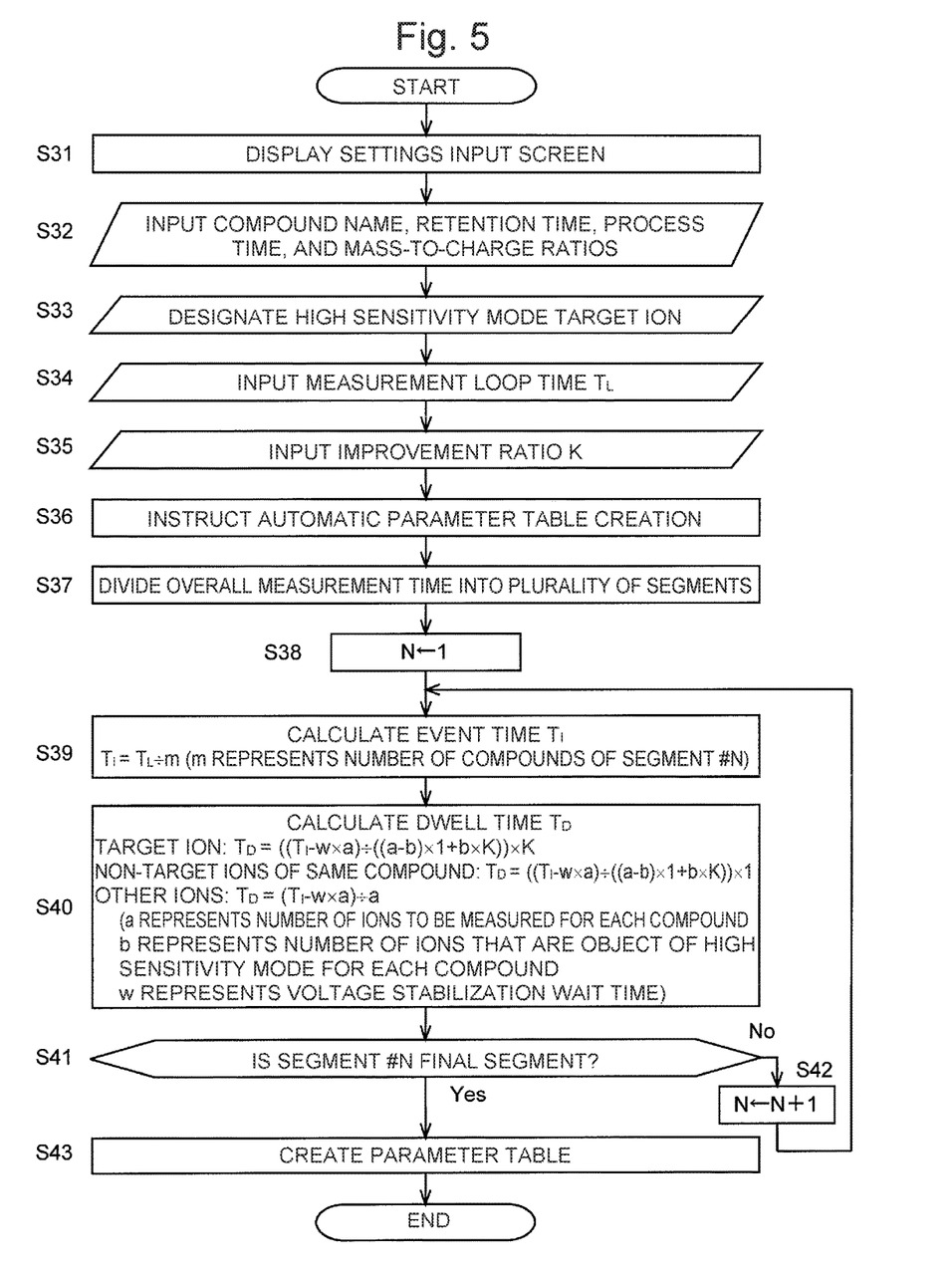
FIG. 5 is a flowchart of operations when executing an automatic parameter table creation process in the LC-MS of a second embodiment.
Figure 6:
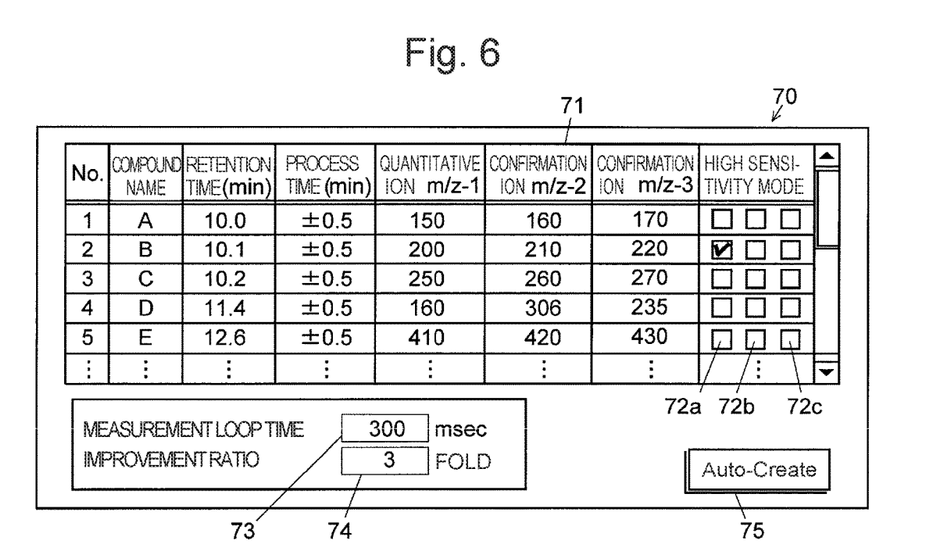
FIG. 6 is a diagram illustrating an example of a settings input screen on the LC-MS of the second embodiment.
Figure 7:
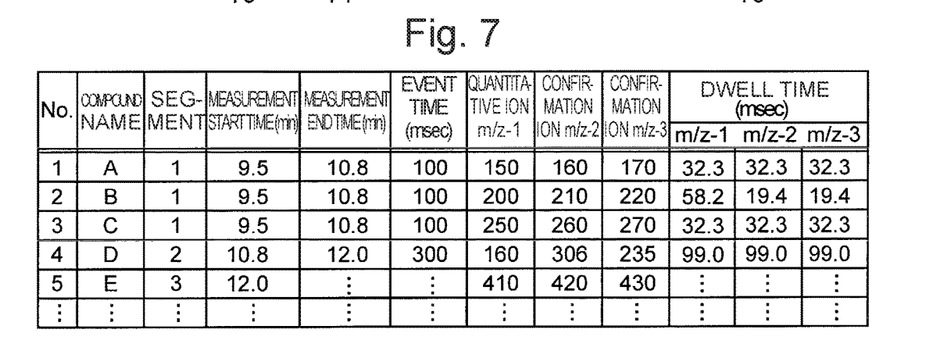
FIG. 7 is a diagram illustrating a parameter table created by executing an automatic parameter table creation process in the LC-MS of the second embodiment based on setting contents that are set using the settings input screen shown in FIG. 6.

Next, an LC-MS according to a second embodiment of the present invention will be described referring to FIG. 5 to FIG. 7. FIG. 5 is a flowchart illustrating processing procedures according to a parameter table creation program of the LC-MS of the present embodiment. FIG. 6 illustrates an example of a settings input screen in the present embodiment. FIG. 7 is a diagram illustrating a parameter table created by executing an automatic parameter table creation process in the LC-MS of the present embodiment based on the setting contents illustrated in FIG. 6. The LC-MS according to the present embodiment has the same configuration as the LC-MS according to the first embodiment that is shown in FIG. 1, and only the operations of the settings input acceptance unit 55, the event time determination unit 57 and the dwell time determination unit 58 of the parameter table creation program 52 are different from the first embodiment.

In the present embodiment, the objects of the high sensitivity mode are designated in ion units, and not in compound units as in the first embodiment. Specifically, in the present embodiment, the analysis operator designates a mass-to-charge ratio to be taken as an object of the high sensitivity mode from among a plurality of mass-to-charge ratios to be measured for each target compound. The parameter table creation process in the present embodiment is described in detail hereunder.

First, when the analysis operator starts the parameter table creation program 52 by performing a predetermined operation using the input unit 43, the settings input acceptance unit 55 displays a settings input screen 70 on the screen of the display unit 44 (step S31). An example of the settings input screen 70 in the present embodiment is illustrated in FIG. 6. A compound table display field 71, a measurement loop time input field 73 and an improvement ratio input field 74 are provided on the settings input screen 70. In a compound table that is displayed in the compound table display field 71, similarly to the first embodiment, it is possible to set, for each target compound, the compound name, retention time, process time, and a mass-to-charge ratio (m/z-1) of one quantitative ion and mass-to-charge ratios (m/z-2 and m/z-3) of two confirmation ions that are to be measured for the compound in question. In addition, as a characteristic element of the present embodiment, in the compound table, check boxes 72a to 72c are provided for individually designating whether or not each of the plurality of mass-to-charge ratios to be measured for the respective compounds is to be taken as an object of the high sensitivity mode. The three check boxes 72a to 72c provided in each row in FIG. 6 correspond to, in order from the left side, the mass-to-charge ratio (m/z-1) of the quantitative ion, the mass-to-charge ratio (m/z-2) of the first confirmation ion and the mass-to-charge ratio (m/z-3) of the second confirmation ion.

Similarly to the first embodiment, the analysis operator inputs the compound name, retention time, process time and mass-to-charge ratios (m/z-1, m/z-2 and m/z-3) of each target compound in the compound table through the input unit 43 (step S32). In the example illustrated in FIG. 6, the same contents as in the compound table illustrated in FIG. 3 and FIG. 8 are input for these items. Further, from among the check boxes 72a to 72c corresponding to the mass-to-charge ratio (m/z-1) of the quantitative ion and the mass-to-charge ratios (m/z-2 and m/z-3) of the confirmation ions of the respective target compounds, the analysis operator checks a check box for a mass-to-charge ratio of an ion to be taken as an object of the high sensitivity mode (step S33), and then also inputs appropriate numerical values in the measurement loop time input field 73 and the improvement ratio input field 74, respectively (steps S34 and S35). In the example in FIG. 6, the mass-to-charge ratio of the quantitative ion of the compound B is selected as the object of the high sensitivity mode, the measurement loop time $T_L$ is set to 300 [msec], and the improvement ratio K is set to 3 [-fold]. In the present embodiment, the term "improvement ratio" refers to a ratio between the dwell time of an ion that is an object of the high sensitivity mode and the dwell time of the other ions among the plurality of ions to be measured with respect to a certain compound, and means that, for example, when the improvement ratio K is "3", the dwell time for the ion that is the object of the high sensitivity mode will be made three times longer than the dwell time for the other ions.

When the analysis operator clicks on an "Auto-Create" button 75 in a state in which the above described input of settings has been completed, the contents that were set on the settings input screen 70 are stored in the settings contents storage unit 53, and an instruction is issued to execute a process to automatically create a parameter table (step S36). As a result, first, the segment setting unit 56 sets segments in a similar manner to the first embodiment (step S37).

Next, the parameter table creation program 52 sets the variable N to 1 (step S38), and calculates the event time $T_I$ using the event time determination unit 57 (step S39). In the present embodiment, the event time $T_I$ that is the measurement time per compound is determined by dividing the measurement loop time $T_L$ by the number of compounds m assigned to the segment #N (that is, $T_I = T_L \div m$). In the example illustrated in FIG. 6, the measurement loop time $T_L$ is 300 [msec], and three compounds, namely, compounds A to C, are assigned to segment #1. Accordingly, the event time $T_I$ for each of the compounds A to C is 300÷3=100 [msec]. Further, since only one compound (compound D) is assigned to segment #2, the event time $T_I$ relating to the pertinent compound is 300÷1=300 [msec].

Next, the dwell time determination unit 58 calculates a dwell time (data accumulation time period) for the plurality of ions to be measured with respect to each target compound (step S40). At this time, the dwell time determination unit 58 performs a calculation based on, for example, the following equations so that the dwell time $T_D$ of ions designated for analysis in the high sensitivity mode becomes longer by approximately a multiple of K ("K" represents the improvement ratio) relative to the dwell time $T_D$ of the other ions.

High sensitivity mode target ion: $T_D = ((T_I - w \times a) \div ((a - b) \times 1 + b \times K)) \times K$ Non-target ions of the same compound: $T_D=((T_r-w \times a) \div ((a-b) \times 1 + b \times K)) \times 1$ Other ions: $T_D=(T_r-w \times a) \div a$ (where "a" represents the number of ions to be measured, "b" represents the number of ions that are an object of the high sensitivity mode, and "w" represents the voltage stabilization wait time)

The above term "non-target ions of the same compound" refers to, in a case where at least one of a plurality of ions to be measured with respect to a certain compound is designated as an object of the high sensitivity mode, the remaining ions (ions that are not designated as the object of the high sensitivity mode) among the plurality of ions to be measured with respect to the same compound. In the case of the compound table shown in FIG. 6, the two confirmation ions (m/z–2 and m/z–3) of the compound B correspond to the aforementioned "non-target ions of the same compound". Further, the aforementioned "other ions" is a term that, in a case where none of a plurality of ions to be measured with respect to a certain compound is designated as an object of the high sensitivity mode, refers to the plurality of ions. In the case of the compound table illustrated in FIG. 6, the quantitative ion (m/z–1) and the confirmation ions (m/z–2 and m/z–3) of each of the compounds A, C, D and E correspond to "other ions".

In the example in FIG. 6, because there are three ions (quantitative ion m/z–1, confirmation ion m/z–2, and confirmation ion m/z–3) that are measurement target ions with respect to a single compound, and the improvement ratio K is 3 [-fold], if it is assumed that the voltage stabilization wait time is 1 [msec], the dwell time $T_D$ for the quantitative ion (m/z–1) of compound B that is a "high sensitivity mode target ion" is $((100-1 \times 3) \div ((3-1) \times 1 + 1 \times 3)) \times 3 = 58.2$ [msec].

Further, the dwell time $T_D$ for the confirmation ions (m/z–2, m/z–3) of compound B that are "non-target ions of the same compound" is $((100-1 \times 3) \div ((3-1) \times 1 + 1 \times 3)) \times 1 = 19.4$ [msec], respectively. In addition, the dwell time for the quantitative ions and confirmation ions of the compounds A and C that are "other ions" is $(100-1 \times 3) \div 3 = 32.3$ [msec]. Further, the dwell time $T_D$ for the respective ions of compound D belonging to segment #2 is $(300-1 \times 3) \div 3 = 99$ [msec].

In this connection, in step S40, if all of a plurality of ions to be measured for the same compound are ions that are an object of the high sensitivity mode, the dwell times of these ions will all be equal, and it will not be possible to obtain the effect of the high sensitivity mode. Therefore, to prevent such a designation, when the analysis operator designates ions to be objects of the high sensitivity mode in step S33, it is desirable that, with respect to the check boxes 72a to 72c provided on the settings input screen 70, at a time point at which a predetermined number (one or two) of the check boxes in a single row are checked, the remaining check box (or check boxes) in the same row is disabled (for example, the check box isn't checked even if the analysis operator clicks on the check box).

Next, the parameter table creation program 52 determines whether or not the segment #N is the final segment (step S41). If the segment #N is not the final segment, the parameter table creation program 52 increments the variable N (step S42) and returns to step S39. Accordingly, processing is executed in time order for all of the segments that were set in step S37, and when the final segment is reached, the result determined in step S41 is "Yes". Thereupon, a parameter table that includes the event times and dwell times calculated as described above is created (step S43), and is stored in the parameter table storage unit 54.

FIG. 7 is an example of a parameter table that is automatically created based on the contents of the settings input screen 70 shown in FIG. 6. As will be understood from the example illustrated in FIG. 7, in the present embodiment, dwell times are individually determined for each of a plurality of ions to be measured for each compound. Further, among the three ions to be measured for compound B, the dwell time for the quantitative ion (m/z–1) that is designated as an object of the high sensitivity mode is longer than the dwell time for the remaining ions (confirmation ions m/z–2 and m/z–3). In the example illustrated in FIG. 7, the total of the dwell times $T_D$ and the voltage stabilization wait time w for compound B is $58.2+19.4+19.4+1 \times 3=100$ [msec], which is equal to the event time T for the pertinent compound set in step S39. Further, the ratio between the dwell time of the ion that is an object of the high sensitivity mode with respect to compound B and the dwell time of the other ions with respect to the pertinent compound is $58.2 \div 19.4 = 3$, which is equal to the improvement ratio K set in step S35. Thus, according to the LC-MS of the present embodiment, by performing a simple operation to designate ions that are objects of the high sensitivity mode and also input the improvement ratio on the settings input screen 70, the analysis operator can automatically set the dwell time of some ions so as to be longer than the dwell time of other ions without affecting the event time of the respective compounds. Therefore, for example in the case of a compound for which the sensitivity is poor, by setting the quantitative ion thereof as an object of the high sensitivity mode, the dwell time of a confirmation ion that is not used for quantitative determination can be shortened, and the dwell time of the quantitative ion can be increased by a corresponding amount and thus highly accurate quantitative determination can be performed.

Although in the present embodiment a configuration is adopted in which, in the compound table display field 71 of the settings input screen 70, a number of check boxes that is the same as the number of ions to be measured are provided in each row of the compound table, the present invention is not limited thereto, and a configuration may also be adopted in which only one check box is provided in each row of the compound table, and only the quantitative ion is automatically taken as the object of the high sensitivity mode among the plurality of ions to be measured with respect to a compound for which the check box is checked. In this case, in step S31 in FIG. 5, the settings input screen 60 that is the same as in FIG. 3 is displayed on the display unit 44. Further, in step S33, the analysis operator checks any of the check boxes 62 on the settings input screen 70, so that the quantitative ion of the compound corresponding to the row on which the pertinent check box is provided is designated as an ion to be the object of the high sensitivity mode. Thereafter, setting of segments (step S37), calculation of event times (step S39), and calculation of dwell times (step S40) and the like are executed in the same manner as described above and a parameter table as shown in FIG. 7 is created.

Although the modes for implementing the present invention have been described above by way of the embodiments, it should be noted that the present invention is not limited to the foregoing embodiments, and it is evident that any modification, adjustment, or addition made within the spirit of the present invention is also included in the scope of the claims of the present application. For example, although in the LC-MS of the above described embodiments, the MS unit 20 is a single quadrupole mass spectrometer, naturally the present invention is also applicable to the case of an LC-MS/MS including an MS unit 20 which is a triple quadrupole mass spectrometer in which MRM measurement is performed which requires setting of measurement conditions, such as the elution time range and the mass-to-charge ratio to be measured for each compound, as with SIM measurement. Further, it will be evident that the present invention is also applicable to a GC-MS and a GC-MS/MS which uses a GC instead of an LC.

REFERENCE SIGNS LIST

10 . . . LC Unit
20 . . . MS Unit
25 . . . Quadrupole Mass Filter
26 . . . Detector
40 . . . Control/Processing Unit
41 . . . CPU
42 . . . Memory
43 . . . Input Unit
44 . . . Display Unit
45 . . . Interface
50 . . . Storage Unit
52 . . . Parameter Table Creation Program
53 . . . Settings Contents Storage Unit
54 . . . Parameter Table Storage Unit
55 . . . Settings Input Acceptance Unit
56 . . . Segment Setting Unit
57 . . . Event Time Determination Unit
58 . . . Dwell Time Determination Unit
60, 70, 80 . . . Settings Input Screen
61, 71, 81 . . . Compound Table Display Field
62, 72a to 72c . . . Check Box
63, 73, 83 . . . Measurement-Loop Time Input Field
64, 74 . . . Improvement Ratio Input Field

The invention claimed is:

1. A chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:
   a) compound table holding means for storing a compound table including at least information identifying, for each compound to be measured, an elution time range and mass-to-charge ratios of one or more ions to be measured;
   b) high-sensitivity analysis designation acceptance means for allowing an analysis operator to designate whether or not to perform a high-sensitivity analysis with respect to each of the compounds included in the compound table;
   c) segment setting means for determining a boundary at a time point where the elution time ranges of the compounds included in the compound table do not overlap with each other to set segments each of which is a measurement time unit, and assigning one or more compounds to be measured to each of the segments;
   d) event time determination means for, for each of the segments set by the segment setting means, determining an event time, which is a measurement time for each compound, by dividing a measurement loop time, which is a previously given measurement point time interval for each ion, according to a number of compounds assigned to the pertinent segment; and
   e) dwell time determination means for determining a dwell time, which is a data collection time for each mass-to-charge ratio, based on the event time determined by the event time determination means and a number of ions to be measured for each compound;
   wherein, in a case where a compound that is an object of the high-sensitivity analysis is included among the compounds assigned to the pertinent segment, the event time determination means divides the measurement loop time so that a ratio of an event time of the compound that is the object of the high-sensitivity analysis to an event time of other compounds assigned to the same segment is a predetermined ratio.

2. The chromatograph mass spectrometer according to claim 1, wherein the high-sensitivity analysis designation acceptance means further allows an analysis operator to designate the ratio.

3. A non-transitory computer readable medium recording a program for causing a computer to function as each means of the chromatograph mass spectrometer according to claim 1.

4. A chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:
   a) compound table holding means for storing a compound table including at least information identifying, for each compound to be measured, an elution time range and mass-to-charge ratios of one or more ions to be measured;
   b) high-sensitivity analysis designation acceptance means for allowing an analysis operator to designate whether or not to perform a high-sensitivity analysis with respect to each of the mass-to-charge ratios included in the compound table;
   c) segment setting means for determining a boundary at a time point where the elution time ranges of the compounds included in the compound table do not overlap with each other to set segments each of which is a measurement time unit, and assigning one or more compounds to be measured to each of the segment;
   d) event time determination means for, for each of the segments set by the segment setting means, determining an event time, which is a measurement time for each compound, based on a measurement loop time, which is a previously given measurement point time interval for each ion, and a number of compounds assigned to the pertinent segment; and
   e) dwell time determination means for determining a dwell time, which is a data collection time for each mass-to-charge ratio, by dividing the event time determined for each of the compounds by the event time determination means, according to a number of mass-to-charge ratios to be measured for a compound corresponding to the event time;

wherein, in a case where a mass-to-charge ratio that is designated as an object of the high-sensitivity analysis is included in the mass-to-charge ratios to be measured for the compound corresponding to the event time, the dwell time determination means divides the event time so that a ratio of a dwell time of the mass-to-charge ratio that is designated as the object of the high-sensitivity analysis to a dwell time of other mass-to-charge ratios to be measured with respect to the same compound is a previously given ratio.

5. The chromatograph mass spectrometer according to claim 4, wherein the high-sensitivity analysis designation acceptance means further allows an analysis operator to designate the ratio.

6. A non-transitory computer readable medium recording a program for causing a computer to function as each means of the chromatograph mass spectrometer according to claim 4.

7. A chromatograph mass spectrometer combining a chromatograph for separating compounds in a sample in a temporal direction and a mass spectrometer for separating ions originating from the compounds separated by the chromatograph according to mass-to-charge ratios and detecting the ions, the mass spectrometer performing selected ion monitoring (SIM) measurement or multiple reaction monitoring (MRM) measurement with respect to mass-to-charge ratios of one or more specific ions at around a chromatogram peak corresponding to a target compound, the chromatograph mass spectrometer comprising:

a) compound table holding means for storing a compound table including at least information identifying, for each compound to be measured, an elution time range, a mass-to-charge ratio of a quantitative ion to be measured, and a mass-to-charge ratio of a confirmation ion to be measured;

b) high-sensitivity analysis designation acceptance means for allowing an analysis operator to designate whether or not to perform a high-sensitivity analysis with respect to each of the compounds included in the compound table;

c) segment setting means for determining a boundary at a time point where the elution time ranges of each of the compounds included in the compound table do not overlap with each other to set segments each of which is a measurement time unit, and assigning one or more compounds to be measured to each of the segments;

d) event time determination means for, for each of the segments set by the segment setting means, determining an event time, which is a measurement time for each compound, based on a measurement loop time, which is a previously given measurement point time interval for each ion, and a number of compounds assigned to the pertinent segment; and e) dwell time determination means for determining a dwell time, which is a data collection time for each mass-to-charge ratio, by dividing the event time determined for each of the compounds by the event time determination means, according to a number of mass-to-charge ratios to be measured for a compound corresponding to the event time;

wherein, in a case where the compound corresponding to the event time is designated as an object of the high-sensitivity analysis, the dwell time determination means divides the event time so that a ratio of a dwell time of a mass-to-charge ratio of a quantitative ion to be measured with respect to the compound to a dwell time of a mass-to-charge ratio of a confirmation ion to be measured with respect to the compound becomes a previously given ratio.

8. The chromatograph mass spectrometer according to claim 7, wherein the high-sensitivity analysis designation acceptance means further allows an analysis operator to designate the ratio.

9. A non-transitory computer readable medium recording a program for causing a computer to function as each means of the chromatograph mass spectrometer according to claim 7.

* * * * *